(12) United States Patent
Folan et al.

(10) Patent No.: US 10,470,904 B2
(45) Date of Patent: Nov. 12, 2019

(54) STENT RETRIEVAL SYSTEM

(71) Applicant: BOSTON SCIENTIFIC SCIMED, INC., Maple Grove, MN (US)

(72) Inventors: Martyn G. Folan, Loughrea (IE);
Thomas M. Keating, Galway (IE);
Gerasimos Rigalos, Galway (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 0 days.

(21) Appl. No.: 15/596,472

(22) Filed: May 16, 2017

(65) Prior Publication Data
US 2017/0333230 A1 Nov. 23, 2017

Related U.S. Application Data

(60) Provisional application No. 62/338,044, filed on May 18, 2016.

(51) Int. Cl.
*A61F 2/90* (2013.01)
*A61F 2/95* (2013.01)

(52) U.S. Cl.
CPC ........ *A61F 2/90* (2013.01); *A61F 2/95* (2013.01); *A61F 2002/9522* (2013.01); *A61F 2002/9528* (2013.01); *A61F 2002/9534* (2013.01); *A61F 2210/0014* (2013.01); *A61F 2210/0076* (2013.01); *A61F 2220/0058* (2013.01); *A61F 2230/001* (2013.01); *A61F 2230/005* (2013.01); *A61F 2250/0018* (2013.01); *A61F 2250/0039* (2013.01); *A61F 2250/0067* (2013.01); *A61F 2250/0098* (2013.01)

(58) Field of Classification Search
USPC .................................................. 623/1.1–3.1
See application file for complete search history.

(56) References Cited

U.S. PATENT DOCUMENTS

| | | |
|---|---|---|
| 5,474,563 A | 12/1995 | Myler et al. |
| 5,941,895 A | 8/1999 | Myler et al. |
| 6,241,757 B1 | 6/2001 | An et al. |
| 6,569,181 B1 | 5/2003 | Burns |
| 6,626,936 B2 | 9/2003 | Stinson |
| 6,663,663 B2 | 12/2003 | Kim et al. |
| 6,821,291 B2 | 11/2004 | Bolea et al. |
| 7,101,392 B2 | 9/2006 | Heath |
| 7,462,192 B2 | 12/2008 | Norton et al. |
| 7,655,039 B2 | 2/2010 | Leanna et al. |
| 8,197,529 B2 | 6/2012 | Cully et al. |
| 8,623,071 B2 | 1/2014 | Lundkvist et al. |
| 8,784,473 B2 | 7/2014 | Tupil et al. |
| 8,926,686 B2 | 1/2015 | King |
| 9,265,634 B2 | 2/2016 | Brady et al. |
| 2006/0190075 A1 | 8/2006 | Jordan et al. |

(Continued)

*Primary Examiner* — Yashita Sharma
(74) *Attorney, Agent, or Firm* — Seager, Tufte & Wickhem, LLP

(57) ABSTRACT

A braided stent having a plurality of retrieval and/or repositioning levers includes a stent body formed of a plurality of wires interbraided in a braided pattern. The repositioning and/or retrieval levers have a loop portion extending radially away from the stent body and first and second legs extending along the stent body. The levers are configured to be actuated radially inward toward the central longitudinal axis of the stent by a radially inwardly directed force to radially collapse the stent.

13 Claims, 8 Drawing Sheets

(56) References Cited

U.S. PATENT DOCUMENTS

| | | |
|---|---|---|
| 2006/0276887 A1 | 12/2006 | Brady et al. |
| 2011/0071613 A1 | 3/2011 | Wood et al. |
| 2012/0095543 A1 | 4/2012 | Pal |
| 2013/0144372 A1 | 6/2013 | Wood et al. |
| 2013/0197623 A1* | 8/2013 | McHugo ............ A61F 2/852 623/1.18 |
| 2013/0245745 A1 | 9/2013 | Vong et al. |
| 2014/0074220 A1 | 3/2014 | Clerc et al. |
| 2014/0081382 A1 | 3/2014 | Leanna et al. |
| 2014/0156023 A1 | 6/2014 | Blackmon |
| 2014/0243992 A1 | 8/2014 | Walsh et al. |
| 2015/0134074 A1 | 5/2015 | Walsh et al. |
| 2015/0282922 A1 | 10/2015 | Hingston et al. |
| 2015/0290005 A1 | 10/2015 | Wainwright et al. |
| 2017/0079812 A1* | 3/2017 | Lam ..................... A61F 2/90 |

\* cited by examiner

STENT RETRIEVAL SYSTEM

CROSS REFERENCE TO RELATED APPLICATIONS

This application claims the benefit of U.S. Provisional Patent Application Ser. No. 62/338,044, filed on May 18, 2016, the disclosure of which is incorporated herein by reference.

TECHNICAL FIELD

The present invention relates to devices, methods and systems for retrieval and/or repositioning of an implanted stent. More particularly, the present invention relates to implantable stents having stent retrieval levers for easy retrieval and/or repositioning of the implanted stent.

BACKGROUND

An intraluminal prosthesis is a medical device used in the treatment of diseased bodily lumens. One type of intraluminal prosthesis used in the repair and/or treatment of diseases in various body vessels is a stent. A stent is a generally longitudinal tubular device formed of biocompatible material which is useful to open and support various lumens in the body. For example, stents may be used in the vascular system, urogenital tract, gastrointestinal tract, esophageal tract, tracheal/bronchial tubes and bile duct, as well as in a variety of other applications in the body.

Stents generally include an open flexible configuration. This configuration allows the stent to be inserted through curved body lumens. Furthermore, this configuration allows the stent to be configured in a radially compressed state for intraluminal delivery. Once properly positioned adjacent the target location in the body lumen, the stent is radially expanded so as to support and reinforce the body lumen. Radial expansion of the stent may be accomplished by inflation of a balloon attached to the delivery device or the stent may be of the self-expanding variety which will automatically radially expand once unconstrained by the delivery device.

Various techniques or systems have been proposed for retrieving and/or repositioning an implanted stent. For example, some stents may include a retrieval suture or wire located at one end of the stent. The retrieval suture or wire may be engaged by a retrieval tool, and, upon twisting or axially pulling retrieval suture or wire, the stent is contracted thereby allowing retrieval of the stent.

Prior retrieval systems often require certain user-sensitive techniques, such as twisting or turning in order to reposition or remove the stent. Moreover, the retrieval suture or wire that allows the stent to purse down or reduce in diameter generally results in a reduction in diameter over a relatively short distance from the end of the stent that the retrieval suture or wire is located and does not cause the stent to be reduced in diameter along a majority of the length of the stent. The removal of the stent is then reliant on an extraction force sufficient to overcome the frictional resistance between the stent and the intimal wall of the body lumen.

Accordingly, there is an ongoing need to provide alternative repositioning and/or retrieval mechanisms for an intraluminal prosthesis, such as a stent.

SUMMARY

The present disclosure is directed to various embodiments of a stent, for example a braided stent, having an integral repositioning and/or retrieval mechanism.

In a first example, a stent includes a tubular body formed of one or more interwoven wires. The tubular body has a lumen extending therethrough from a first open end of the tubular body to a second open end of the tubular body. The tubular body has a length measured from the first open end to the second open end and a longitudinal axis extending therebetween. The stent further includes a plurality of repositioning and/or retrieval levers spaced apart circumferentially around the first open end and extending beyond the first open end. The repositioning and/or retrieval levers extend radially outward from the tubular body. Each repositioning and/or retrieval lever has first and second legs extending along a portion of the tubular body toward the second open end. The repositioning and/or retrieval levers are configured to translate a radially inward squeezing force applied to the repositioning and/or retrieval levers at a location beyond the first open end to a radially inward contracting force along the first and second legs extending along the tubular body.

Alternatively or additionally, in another example, the plurality of repositioning and/or retrieval levers are separate elements from the interwoven wires forming the tubular body.

Alternatively or additionally, in another example, the plurality of repositioning and/or retrieval levers include three levers attached to and extending beyond the first open end of the tubular body.

Alternatively or additionally, in another example, each of the plurality of repositioning and/or retrieval levers extends radially outward from the tubular body at an angle of between 20 and 90 degrees from the longitudinal axis.

Alternatively or additionally, in another example, each of the plurality of repositioning and/or retrieval levers extends at an angle of between 30 and 70 degrees from the longitudinal axis.

Alternatively or additionally, in another example, the plurality of repositioning and/or retrieval levers are made of a material having a greater stiffness than a material of the one or more interwoven wires forming the tubular body.

Alternatively or additionally, in another example, the first and second legs of each of the repositioning and/or retrieval levers extend over 25% or more of the length of the tubular body.

Alternatively or additionally, in another example, the first and second legs of each of the repositioning and/or retrieval levers extend substantially over the entire length of the tubular body from the first open end to the second open end.

Alternatively or additionally, in another example, each of the first and second legs of each of the repositioning and/or retrieval levers extends helically along an interwoven wire forming the tubular body.

Alternatively or additionally, in another example, the first leg extends in a first helical direction and the second leg extends in a second helical direction opposite the first helical direction.

Alternatively or additionally, in another example, the first and second legs of each of the repositioning and/or retrieval levers are attached to an outside surface of the tubular body.

Alternatively or additionally, in another example, the first and second legs of each of the repositioning and/or retrieval levers are interwoven through the tubular body.

Alternatively or additionally, in another example, each of the first and second legs of each of the repositioning and/or retrieval levers is attached to an interwoven wire forming the tubular body at a plurality of welds.

In another example, a braided stent includes a plurality of wires interwoven in a braided pattern to form a tubular stent body having a length between opposed atraumatic first and second open ends with each open end having a circumference. The braided stent further includes at least three repositioning and/or retrieval levers attached to the stent body at a plurality of discrete points. The repositioning and/or retrieval levers are spaced apart around the circumference of the first open end. Each repositioning and/or retrieval lever has a loop portion extending radially away from the tubular stent body and first and second legs extending along 25% or more of the length of the tubular stent body.

Alternatively or additionally, in another example, the first and second legs extend helically along interwoven wires of the braided pattern of the tubular stent body.

Alternatively or additionally, in another example, the repositioning and/or retrieval levers are made of a material having a greater stiffness than a material of the interwoven wires forming the tubular stent body.

Alternatively or additionally, in another example, the repositioning and/or retrieval levers extend radially outward from the tubular stent body at an angle of between 30 and 90 degrees from a central longitudinal axis of the tubular stent body.

Alternatively or additionally, in another example, the repositioning and/or retrieval levers are configured to translate a radially inward squeezing force applied to the loop portion of the repositioning and/or retrieval levers at a location beyond the first open end to a radially inward contracting force along the first and second legs extending along the tubular stent body.

Another example is a method of radially collapsing a stent. The method includes applying a radially inward squeezing force to a plurality of repositioning and/or retrieval levers of a stent. The stent includes a tubular body having a first open end and a second open end. The plurality of repositioning and/or retrieval levers are spaced apart circumferentially around the first open end and extend beyond the first open end. The tubular body is formed of one or more interwoven wires. Each repositioning and/or retrieval lever has first and second legs extending along a portion of the tubular body toward the second open end. The radially inward squeezing force is applied to the repositioning and/or retrieval levers at a location beyond the first open end, which is translated to a radially inward contracting force along the first and second legs extending along the tubular body to radially contract the tubular body.

Alternatively or additionally, in another example, the plurality of repositioning and/or retrieval levers are made of a material having a greater stiffness than a material of the one or more interwoven wires forming the tubular body.

The above summary of some embodiments is not intended to describe each disclosed embodiment or every implementation of the present disclosure. The Figures, and Detailed Description, which follow, more particularly exemplify some of these embodiments.

BRIEF DESCRIPTION OF THE DRAWINGS

In the drawings, which are not necessarily drawn to scale, like numerals may describe similar components in different views. The drawings illustrate generally, by way of example, but not by way of limitation, various embodiments discussed in the present document.

Figure 1:
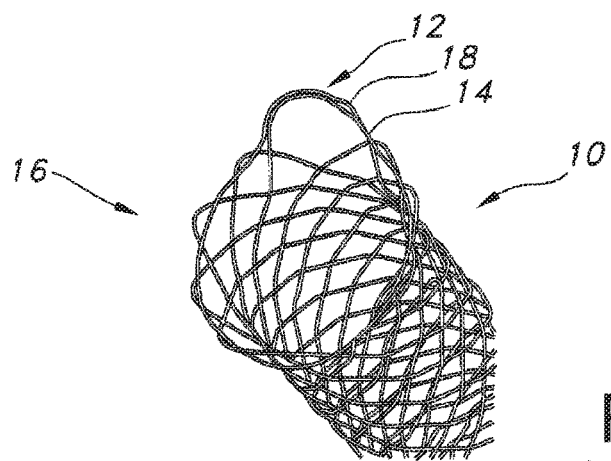
FIG. 1 is a partial expanded view of a stent of the prior art.

While the disclosure is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the disclosure.

DETAILED DESCRIPTION

For the following defined terms, these definitions shall be applied, unless a different definition is given in the claims or elsewhere in this specification.

All numeric values are herein assumed to be modified by the term "about," whether or not explicitly indicated. The term "about" generally refers to a range of numbers that one of skill in the art would consider equivalent to the recited value (i.e., having the same function or result). In many instances, the terms "about" may include numbers that are rounded to the nearest significant figure.

The recitation of numerical ranges by endpoints includes all numbers within that range (e.g. 1 to 5 includes 1, 1.5, 2, 2.75, 3, 3.80, 4, and 5).

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise.

It is noted that references in the specification to "an embodiment", "some embodiments", "other embodiments", etc., indicate that the embodiment described may include one or more particular features, structures, and/or characteristics. However, such recitations do not necessarily mean that all embodiments include the particular features, structures, and/or characteristics. Additionally, when particular features, structures, and/or characteristics are described in connection with one embodiment, it should be understood that such features, structures, and/or characteristics may also be used connection with other embodiments whether or not explicitly described unless clearly stated to the contrary.

The following detailed description should be read with reference to the drawings in which similar structures in different drawings are numbered the same. The drawings, which are not necessarily to scale, depict illustrative embodiments and are not intended to limit the scope of the disclosure.

FIG. 1 depicts a prior art stent 10 including a retrieval and/or repositioning loop 12. The retrieval and/or repositioning loop 12 includes two wires 14, 18 that are circumferentially disposed about the end 16 of stent 10. The two wires 14, 18 are configured to be grasped with a retrieval device such as rat tooth forceps or hooking device and pulled axially to contract the end 16 of the stent 10. The two wires 14, 18 cooperatively work in conjunction with each other to cinch the end 16 of the stent 10 when pulled on by the retrieval device. Further details of this prior art stent 10 with its retrieval and/or repositioning loop 12 may be found in U.S. Patent Application Publication No. 2006/0276887 to Brady et al., the contents of which are incorporated herein by reference. Moreover, another retrieval and/or repositioning loop of a stent is disclosed in U.S. Patent Application Publication No. 2006/0190075 to Jordan et al., the contents of which are incorporated herein by reference.

Figure 2:
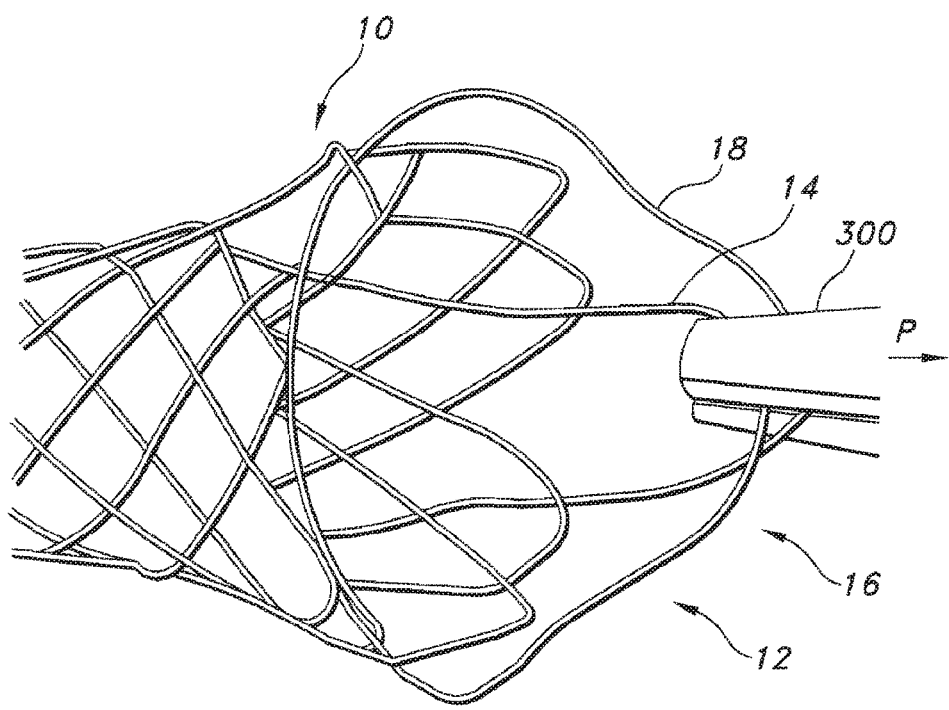
FIG. 2 is another view of the prior art stent of FIG. 1 being pulled by a retrieval device.

FIG. 2 shows the prior art stent 10 being pulled (P) by a retrieval device 300 in an axial direction away from the stent end 16. The retrieval device 300 may hold both wires 14, 18 in a fixed position as it pulls the stent 10. The retrieval device 300 hinders the wires 14, 18 from moving past each other which causes the stent end 16 to remain in a flared state and prevent the wires 14, 18 from fully cinching the stent end 16. Additionally, FIG. 2 shows that the stent 10 body is not fully radially contracted due to the reduced ability of the wires 14, 18 to slide relative to each other.

Thus, there is a need for a retrieval and/or repositioning member that provides both improved stent end cinching and improved stent body radial contraction. Further, there is a need for a retrieval and/or repositioning member that is capable of cinching the end of the stent and radially contracting the stent body using a variety of devices used by a practitioner. Furthermore, there is a need for a retrieval and/or repositioning member that provides for substantially even radial contraction of the stent end and stent body and permits easy access to the retrieval and/or repositioning member by a practitioner.

The present disclosure provides a plurality of retrieval and/or repositioning levers. The retrieval and/or repositioning levers are configured to radially contract the end of the stent and radially contract the stent body. Additionally, the retrieval and/or repositioning levers may provide a structure which has the required tensile strength to prevent fracture or damage to the stent when force is applied to reposition or retrieve the stent.

Figure 3:
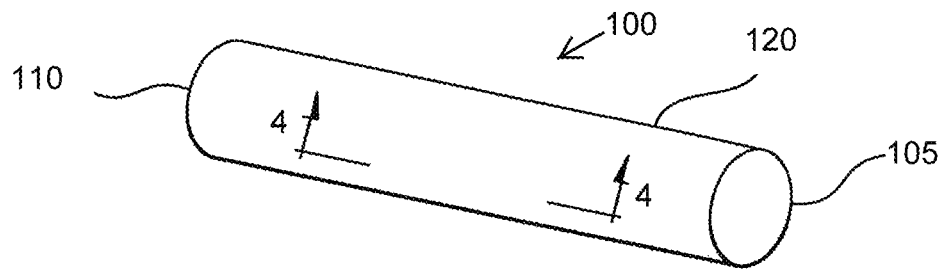
FIG. 3 is a perspective view of a hollow, tubular stent according to the present invention.
Figure 4:
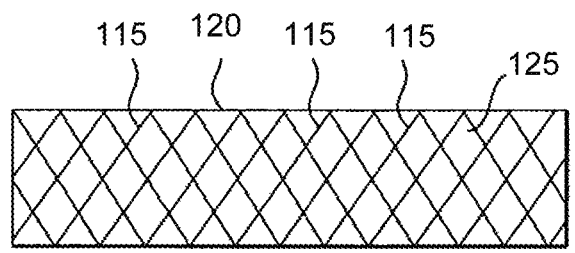
FIG. 4 is an expanded view of a wall portion of the stent of FIG. 3 taken along line 4-4 showing a plurality of interwoven wires forming the tubular body of the stent.

FIG. 3 depicts a stent 100. The stent 100 is a hollow tubular structure having opposed first and second open ends 105, 110 and defines a tubular wall 120 therebetween. A portion of the tubular wall 120 is depicted in FIG. 4 as having a plurality of elongate wires 115 formed into the tubular wall 120. The elongate wires 115 traverse the length of the stent 100 in a direction transverse to the longitudinal length of the stent 100. For example, the elongate wires 115 may extend along the length of the stent 100 in a helical arrangement, with a portion of the elongate wires 115 extending in a first helical direction and a second portion of the elongate wires 115 extending in a second helical direction, opposite the first helical direction. The elongate wires 115 may be interwoven such that wires 115 extending in the first helical direction cross over and/or under wires 115 extending in the second helical direction at a plurality of cross-over points along the length of the stent 100. The wires 115 may traverse the length of the stent 100 in a down-and-back fashion in which a middle portion of each wire 115 forms a bend or loop 130 (see FIG. 5) and end portions on either side of the middle portion extend to the opposite end of the stent 100 and are interwoven to form the tubular body of the stent 100. The elongate wires 115 may be interwoven to form the tubular wall 120 by braiding the wires 115, winding the wires 115, knitting the wires 115, and combinations thereof. Preferably, the wires 115 are braided in a braided pattern 125 to form the tubular wall 120. A useful non-limiting braided pattern includes a one over and one under pattern, but other patterns may suitably be used.

Figure 5:
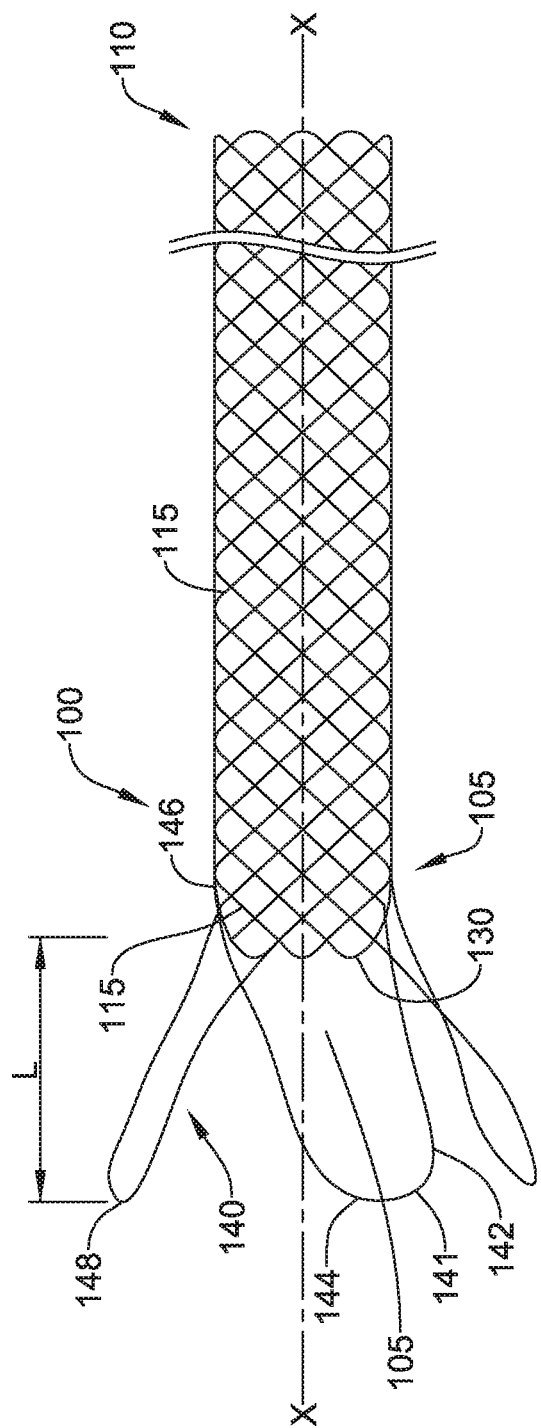
FIG. 5 is a side view of one end of a braided stent with a closed-end loop design and retrieval and/or repositioning levers in accordance with an embodiment of the disclosure.

As depicted in FIG. 5, the stent 100 is desirably an atraumatic stent having no sharp terminating members at one or both of the opposed first and second open ends 105, 110. The elongate wires 115 terminating at the first open end 105 may be mated to form closed loops 130 and adjacently mated wires may be secured to one another by mechanical means, such as welds. The second open end 110 may also include closed loops formed by bending the wires 115 back such that the wires 115 re-enter the braiding pattern of the stent 100. Alternatively, the first open end 105 may include closed loops formed by bending the wires 115 back such that the wires 115 re-enter the braiding pattern of the stent 100 and the second open end 110 may include the ends of the elongate wires 115 which are mated to form closed loops. The positioning of adjacently mated wires to form closed-loop end designs is further described in U.S. Pat. Nos. 7,655,039, and 7,462,192, the contents of all which are incorporated herein by reference.

The stent 100 may include multiple wires 115 of a metal material, such as nitinol or nitinol-containing material, or other nickel-titanium alloy, for example. In some instances, the wires 115 may have a diameter of about 0.011 inches, for example. The number of wires 115 and the diameters of the wires 115, which may be the same or different, depicted in FIG. 5 are not limiting, and other numbers of wires 115 and other wire diameters may suitably be used. Desirably, an even number of wires 115 may be used, for example, from about 10 to about 36 wires 115.

Desirably, the wires 115 are made from any suitable implantable material, including without limitation nitinol, stainless steel, cobalt-based alloy such as Elgiloy®, platinum, gold, titanium, tantalum, niobium, polymeric materials and combinations thereof. Useful and nonlimiting examples of polymeric stent materials include poly(L-lactide) (PLLA), poly(D,L-lactide) (PLA), poly(glycolide) (PGA), poly(L-lactide-co-D,L-lactide) (PLLA/PLA), poly(L-lactide-co-glycolide) (PLLA/PGA), poly(D,L-lactide-co-glycolide) (PLA/PGA), poly(glycolide-co-trimethylene carbonate) (PGA/PTMC), polydioxanone (PDS), Polycaprolactone (PCL), polyhydroxybutyrate (PHBT), poly(phosphazene) poly(D,L-lactide-co-caprolactone) PLA/PCL), poly(glycolide-co-caprolactone) (PGA/PCL), poly (phosphate ester) and the like. Wires made from polymeric materials may also include radiopaque materials, such as metallic-based powders, particulates or pastes which may be incorporated into the polymeric material. For example the radiopaque material may be blended with the polymer composition from which the polymeric wire is formed, and subsequently fashioned into the stent 100 as described herein. Alternatively, the radiopaque material may be applied to the surface of the metal or polymer wire 115 of the stent 100. In either embodiment, various radiopaque materials and their salts and derivatives may be used including, without limitation, bismuth, barium and its salts such as barium sulphate, tantalum, tungsten, gold, platinum and titanium, to name a few. Additional useful radiopaque materials may be found in U.S. Pat. No. 6,626,936, the contents of which are incorporated herein by reference. Metallic complexes useful as radiopaque materials are also contemplated. The stent may be selectively made radiopaque at desired areas along the wire or may be fully radiopaque.

In some instances, the wires 115 may have a composite construction having an inner core of tantalum, gold, platinum, tungsten, iridium or combination thereof and an outer member or layer of nitinol to provide a composite wire for improved radiopacity or visibility. In one example, the inner core may be platinum and the outer layer may be nitinol. The inner core of platinum may represent about at least 10% of the wire 115 based on the overall cross-sectional percentage. Moreover, nitinol that has not been treated for shape memory such as by heating, shaping and cooling the nitinol at its martensitic and austenitic phases, is also useful as the outer layer. Further details of such composite wires may be found in U.S. Pat. No. 7,101,392, the contents of which is incorporated herein by reference. The wires 115 may be made from nitinol, or a composite wire having a central core of platinum and an outer layer of nitinol. Further, the filling weld material, if required by welding processes such as MIG, may also be made from nitinol, stainless steel, cobalt-based alloy such as Elgiloy, platinum, gold, titanium, tantalum, niobium, and combinations thereof.

One of the opposed open ends 105, 110 of the stent 100 may include two or more retrieval and/or repositioning levers 140. It is noted that in some embodiments, both open ends 105, 110 of the stent 100 may include two or more retrieval and/or repositioning levers 140. The retrieval and/or repositioning levers 140 may be uniformly or non-uniformly arranged around the circumference of the open end 105 and/or the open end 110 of the stent 100. In the device illustrated in FIG. 5, the first open end 105 includes three levers 140. The three levers 140 may be uniformly arranged around the circumference of the open end 105. The retrieval and/or repositioning levers 140 may be useful for repositioning and/or retrieval of an implanted or deployed stent 100. The retrieval and/or repositioning levers 140 allow a practitioner to radially contract and move, reposition and/or retrieve the stent 100 within an implanted body lumen (not shown).

The stent retrieval and/or repositioning levers 140 may be made from a biocompatible material, such as a metallic or polymeric material. The stent retrieval and/or repositioning levers 140 may be self-supporting, such that the stent retrieval and/or repositioning levers 140 may be cantilevered and/or extend from the open end 105 of the stent 100 while retaining their shape. In some instances, the stent retrieval and/or repositioning levers 140 may be formed of a metal material, such as the above described materials, including nitinol. The use of a metal material, as compared to other conventional materials such as suture thread, has numerous advantages. For example, the self-supporting nature of the metal material may facilitate maintaining the location/orientation of the retrieval and/or repositioning lever 140. Furthermore, the metal material may permit radially compressive forces applied to the retrieval and/or repositioning levers 140 to be transferred through the retrieval and/or repositioning levers 140 to apply a corresponding radially compressive force to the tubular body of the stent 100 to aid in radially compressing the stent 100.

As depicted in FIG. 5 the stent 100 includes three retrieval and/or repositioning levers 140. In other embodiments, the stent 100 may have two opposing levers, or four or more levers 140 evenly or unevenly spaced around the circumference of the stent 100. For example, a plurality of levers 140 may be provided, generally spaced equally around the circumference of the stent 100.

The retrieval and/or repositioning levers 140 may be formed of a wire 148, for example, extending beyond the closed loops 130 at the end 105 of the tubular body of the stent 100 and along the braid pattern 135 forming the tubular body of the stent 100 for a portion of, or for substantially the entire length of the braided body portion of the stent 100. For example, the retrieval and/or repositioning levers 140 may each include a wire 140 forming two legs 142, 144 that extend beyond the closed loops 130 at the end 105 of the tubular body of the stent 100 and along the braid pattern 125 forming the tubular body of the stent 100. The apex 141 of the legs 142, 144 may be unitarily formed as a curved loop or bend 141 of the wire 148 forming the legs 142, 144 of the retrieval and/or repositioning levers 140, while the bases 146 of each of the legs 142, 144 which extend along body of the stent 100 may extend to an end of the wire 148 forming the legs 142, 144. The bases 146 of each of the legs 142, 144 may not be interconnected with one another. For example, the bases 146 of each of the legs 142, 144 may be spaced away from one another throughout the tubular body of the stent 100.

The wire 140 forming the retrieval and/or repositioning lever 140 may extend beyond the closed loops 130 at the end 105 of the tubular body of the stent 100 for a distance L. In some instances, distance L may be 5% to 50%, 10% to 50%, 10% to 30%, or 5% to 30% of the total stent body length, for example.

Figure 8:
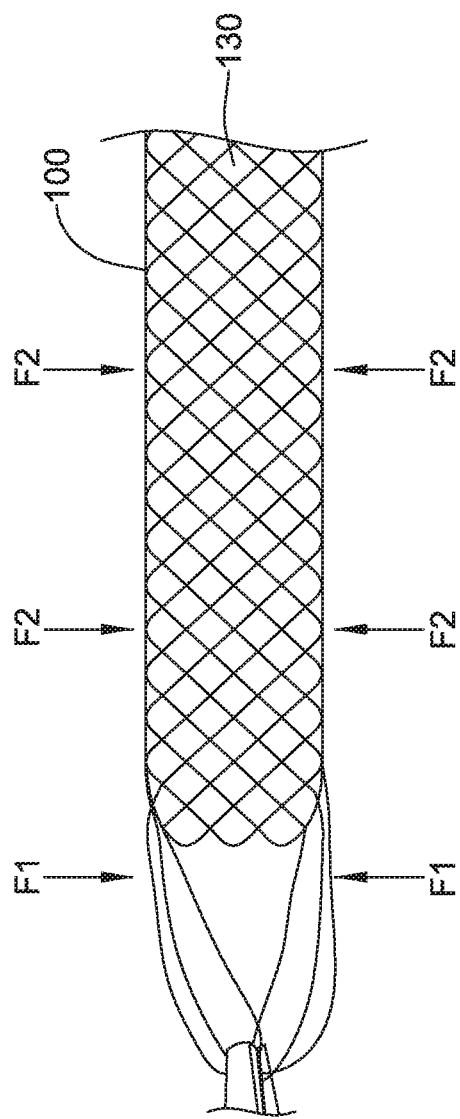
FIG. 8 is a side view of the stent end of FIG. 7 in a retracted or compressed state for retrieval.

In some embodiments, the base 146 of each of the legs 142, 144 may extend separately along the braided pattern 125 of the stent 100. For example, each of the legs 142, 144 may follow adjacent to and be juxtaposed with a filament of the helical braid pattern extending in a helical direction. For instance, the first leg 142 of the retrieval and/or repositioning lever 140 may extend in a first helical direction adjacent to a first filament of the braided pattern 125 and the second leg 144 of the retrieval and/or repositioning lever 140 may extend in a second helical direction, opposite the first helical direction, adjacent to a second filament of the braided pattern 125. The base 146 of the legs 142, 144 may thus extend helically around the circumference of the stent 100 in some instances. Such a configuration may advantageously allow the retrieval and/or repositioning levers 140 to effectively circumscribe the circumferential perimeter of the stent 100, which may facilitate translation of the radially inward pinching or squeezing force F1 to a radially compression force F2 along the length of the stent 100 along which the wires 148 are attached, as shown in FIG. 8. In other embodiments, the base 146 of the legs 142, 144 may extend along the braided tubular body of the stent 100 substantially parallel to the longitudinal axis of the stent 100.

The wire 148 forming the retrieval and/or repositioning lever 140 may be attached to the wires 115 forming the braided pattern 125 of the tubular body of the stent 100 at a plurality of separate locations. The attachment may be via weld, adhesive, wire wrapping, or any other suitable attachment element or mechanism. In the embodiment illustrated in FIG. 7, the wire 148 is welded along an adjacently positioned wire 115 of the braid pattern 125 of the stent 100 at multiple discrete weld locations 150 along the wire 148. The wire 148 may be attached to the inside surface or outside surface of the stent 100. In some embodiments, the wire 148, after forming the loop or bend 141 and legs 142, 144 of the retrieval and/or repositioning lever 140, may enter into and/or follow the normal braiding pattern 125 of the stent 100.

The loop or bend 141 may be bent radially outward from the circumference of the braided tubular body portion of the stent 100, as seen in FIGS. 5-7 and 9. As shown in FIG. 8, when the loops 141 of each of the retrieval and/or repositioning levers 140 are accessed and squeezed radially together, the radially inward squeezing force F1 applied to the levers 140 may be translated to a radially contracting force F2 along the braided tubular body of the stent 100, thereby radially contracting the braided tubular body of the stent 100. The loop or bend region 141 may also be referred to as a grabbing area or portion configured for easy access by a practitioner, for example a practitioner using forceps (not shown) or other retrieval tool.

Further, as wires 148 forming the retrieval and/or repositioning levers 140 are attached to the body of the braided stent 100, the wires 148 forming the legs 142, 144 of the levers 140 extend along a length of the tubular stent body. The legs 142, 144 may extend along the entire or substantially the entire length of the tubular stent body to the opposite end, or partially along the tubular stent body. In some embodiments, the legs 142, 144 extend along 25% or more, 50% or more, or 75% or more of the length of the tubular stent body, or any other distance along the tubular stent body. The retrieval and/or repositioning levers 140 may provide a radially inward contracting action along the longitudinal length of the stent 100 over which the wires 148 extend. The retrieval and/or repositioning levers 140 also facilitate pulling the stent 100 by providing a grasping region at the loops 141. Thus, the squeezing/pinching and pulling of the retrieval and/or repositioning levers 140 may provide for both radially contracting and pulling of the stent 100.

Figure 6:
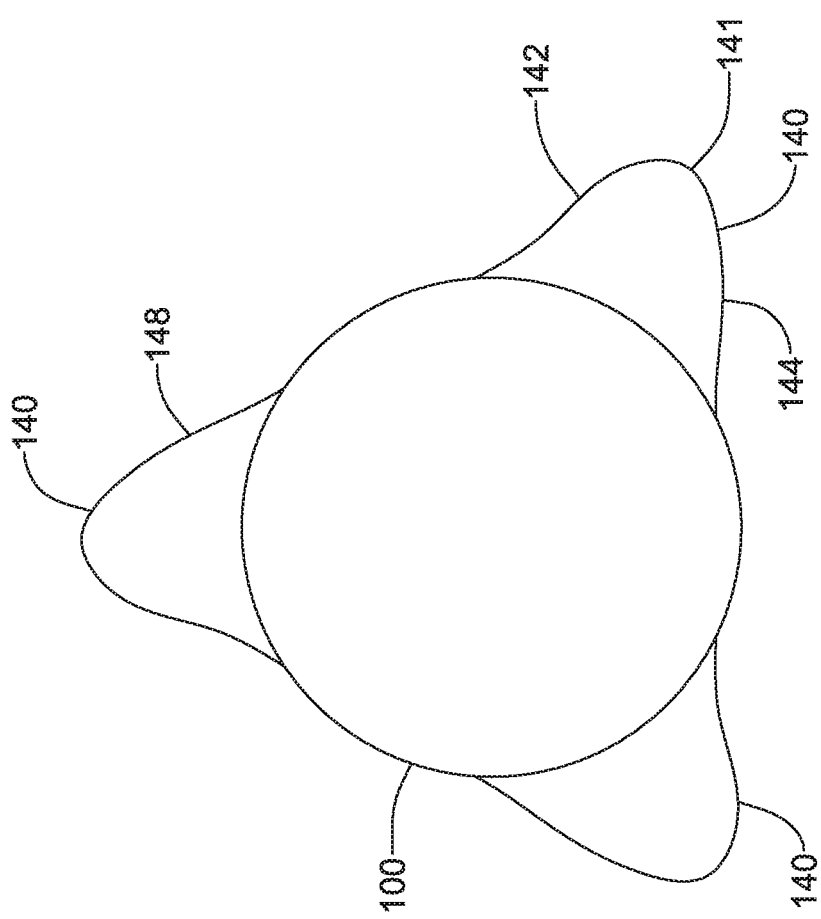
FIG. 6 is an end view of the stent of FIG. 5.
Figure 7:
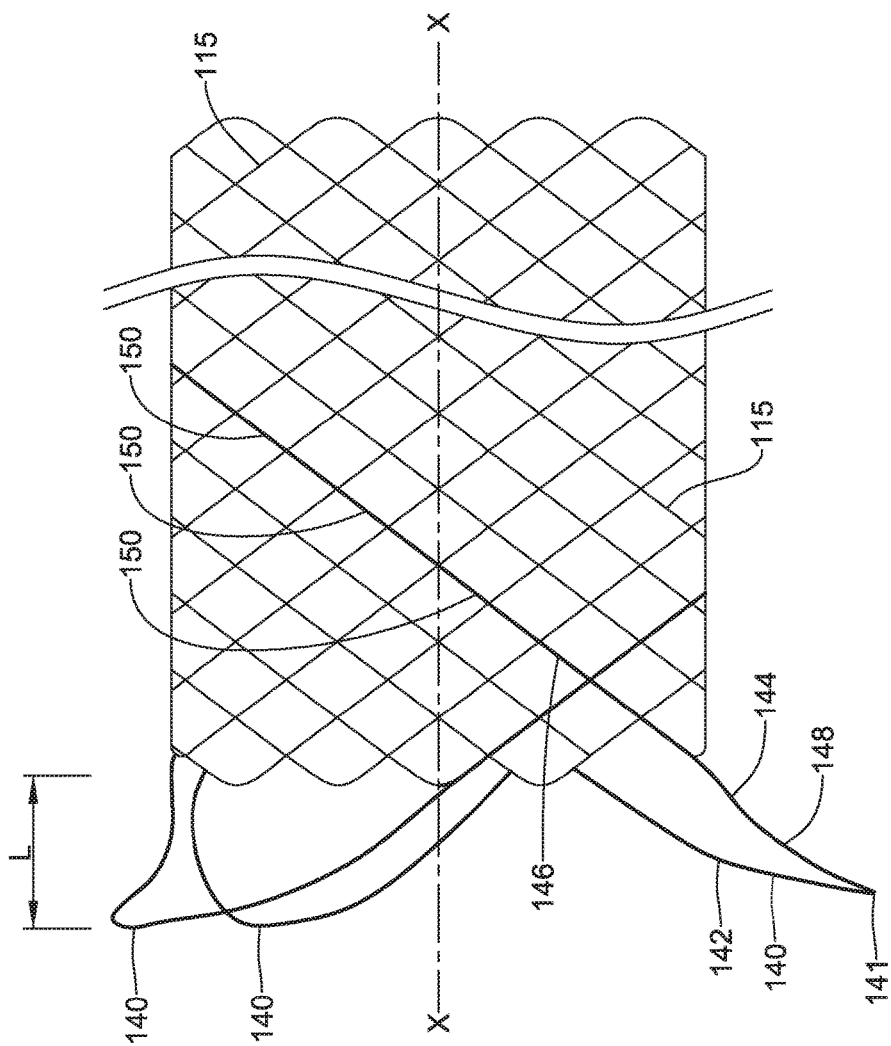
FIG. 7 is a side view of one end of a stent in accordance with another embodiment of the disclosure.

As depicted in FIGS. 5-7 the portion of the retrieval and/or repositioning levers 140 extending beyond the tubular body portion of the stent 100 extend radially outward from the circumference of the tubular body portion of the stent 100. For example, the retrieval and/or repositioning levers 140 may extend radially outward at an angle of between about 20 degrees to about 90 degrees, between about 25 degrees to about 75 degrees, about 30 degrees to about 60 degrees, or about 45 degrees to about 75 degrees from the longitudinal axis X of the stent 100. The angle of the retrieval and/or repositioning levers 140 relative to the axis X may be, for example, 25 degrees or more, 30 degrees or more, 35 degrees or more, 40 degrees or more, 45 degrees or more, 50 degrees or more, 55 degrees or more, 60 degrees or more, 65 degrees or more, 70 degrees or more, 75 degrees or more, 80 degrees or more, or 85 degrees or more degrees, or other desired angle. In the embodiment illustrated in FIG. 5, the retrieval and/or repositioning levers 140 extend at an angle of about 30 degrees from the longitudinal axis X of the stent 100. In the embodiment illustrated in FIG. 7, the retrieval and/or repositioning levers 140 extend at an angle of about 70 degrees from the longitudinal axis X of the stent 100.

The wire 148 forming the retrieval and/or repositioning levers 140 may have the same or different properties than the wires 115 which form the braided stent 100. For example, the wires 148 may be of the same or different stiffness or flexibility, all of which may be tailored for a particular application. In some embodiments, the wire 148 forming a retrieval and/or repositioning lever 140 may be stiffer than the stent wires 115 forming the braided pattern 125 of the tubular body of the stent 100. In some instances, the lever wire 148 may be formed of a different material and/or may have a different diameter than the stent wires 115. In some instances, the lever wire 148 may be stainless steel while the stent wires 115 may be formed of a nickel-titanium alloy, such as nitinol. In some instances, the material forming the lever wires 148 may have a stiffness greater than the material forming the wires 115 of the braided pattern 125 of the stent 100 and/or the material forming the lever wires 148 may have a modulus of elasticity (Young's modulus) greater than the material forming the wires 115 of the braided pattern 125 of the stent 100. The choice of material, wire diameter and pre-treatment of the wires 148, 115 and stent configuration are some of the factors which may be varied to achieve particular stent properties. Additionally, as mentioned herein, the at least one retrieval and/or repositioning lever 140 may also be made radiopaque by various methods, for example with a coating or finish, with a band or as part of the stent material, as further described herein. Color or different finishes may also be added to the retrieval and/or repositioning lever 140 to visually differentiate it from the rest of the stent wires 115.

Figure 9:
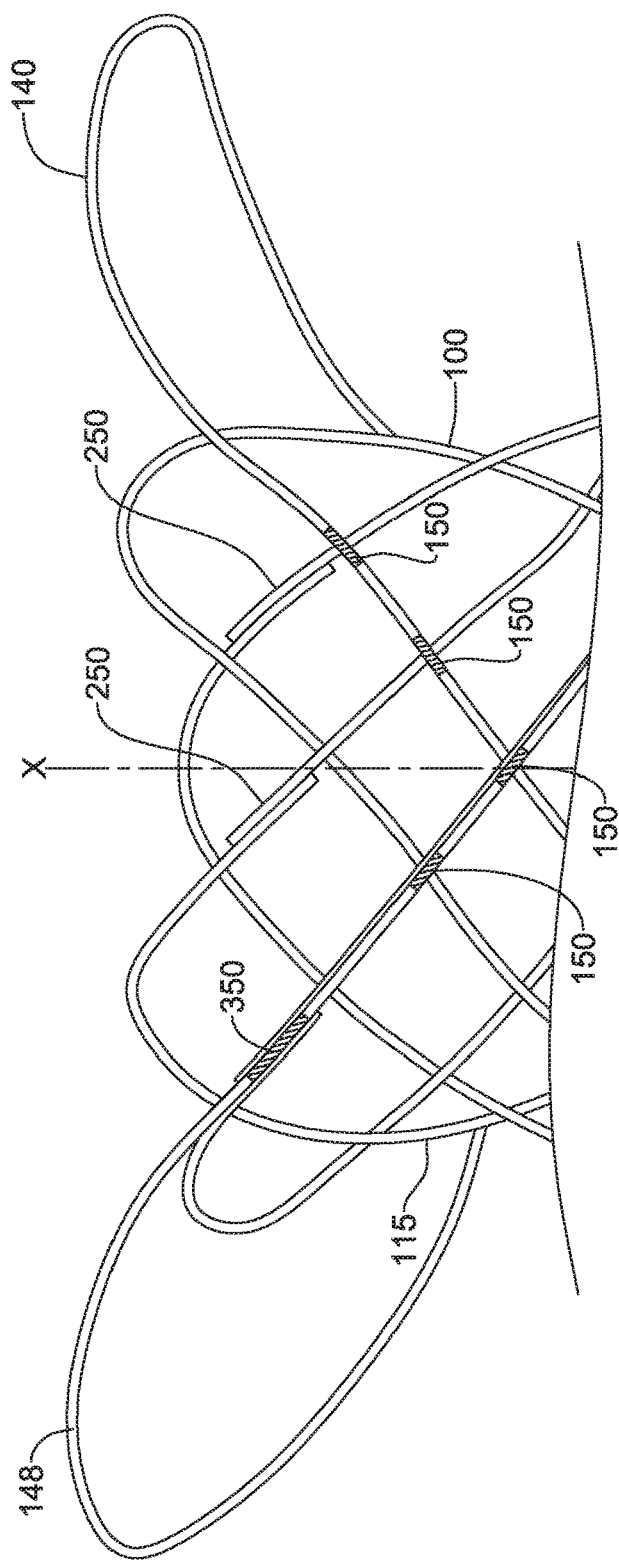
FIG. 9 is a side view of a portion of one end of a stent in accordance with an embodiment of the disclosure.

In one embodiment, one end of the stent 100 may have weld joints 250 attaching ends of two wires 115 of the stent 100 proximate one end of the braided tubular body of the stent 100. In these embodiments, the weld joint 250 may be positioned between the crossings of adjacent wires 115, as shown in FIG. 9. In other embodiments, the weld joint 250 may span a crossing of adjacent wires 115. In FIG. 9, the opposing side of the stent is not shown for clarity. The wires 148 forming the retrieval and/or repositioning levers 140 may be welded to two ends of stent wires 115 at a single weld 350 joining three wires (two ends of stent wires 115 and lever wire 148), or the lever wire 148 may be joined to a single stent wire 115 at a weld 150. In other embodiments, the stent weld joints 250 joining ends of the wires 115 may be at the opposite end from the retrieval and/or repositioning levers 140, and the end of the stent having the retrieval and/or repositioning levers 140 may only include the welds 150 joining the lever wires 148 to the stent wires 115.

Figure 10:
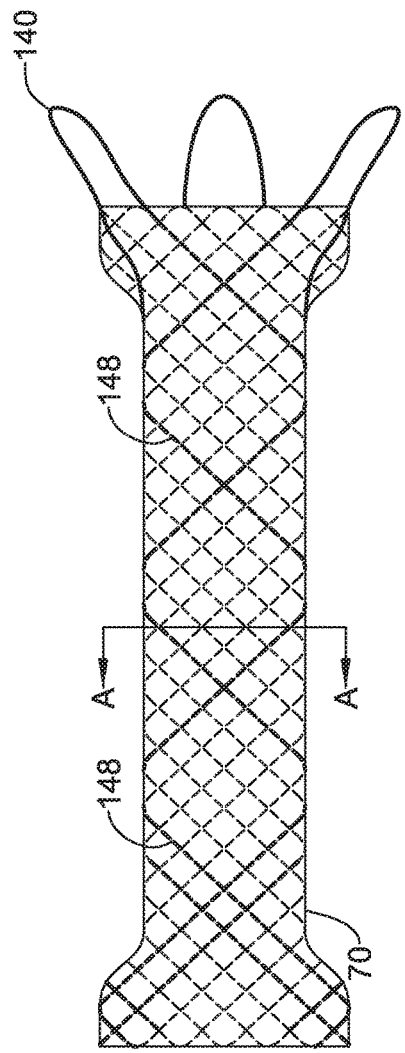
FIG. 10 depicts a stent having a covering in accordance with an embodiment of the disclosure.

As depicted in FIG. 10, in some embodiments the stent 100 may including a covering 70 covering at least a portion of the braided tubular body of the stent 100. For example, the covering 70 may fully cover the entire length of the braided tubular body of the stent 100, forming a fully covered stent in which all of the interstices defined in the braided pattern are covered with the covering 70 to prevent tissue in-growth, or the covering 70 may cover only a portion of the length of the braided tubular body of the stent 100, forming a partially covered stent in which a portion of the interstices defined in the braided pattern remain uncovered to permit tissue in-growth. The retrieval and/or repositioning levers 140 may not be covered by the covering 70, thus remain uncovered. In some instances, the stent 100 may be dipped into a solution of silicone or other polymer to form the covering 70. In other instances, a polymer sheet or tube may be placed around the tubular body and/or within the tubular body to form the covering 70. The coating or covering may be a polymer covering, such as a polytetrafluoroethylene (PTFE) or silicone covering, however other coverings, particularly elastomeric polymers, may be used. Non-limiting examples of useful polymeric materials include polyesters, polypropylenes, polyethylenes, polyurethanes, polynaphthalenes, polytetrafluoroethylenes, expanded polytetrafluoroethylene, silicone, and combinations and copolymers thereof.

Figure 12:
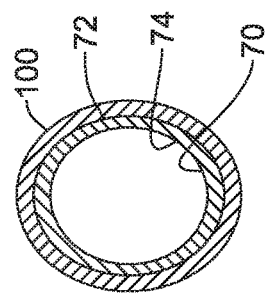
FIG. 12 is an alternative cross-sectional view of the stent of FIG. 10 taken along line A-A showing an inner covering disposed within the tubular body of the stent.
Figure 11:
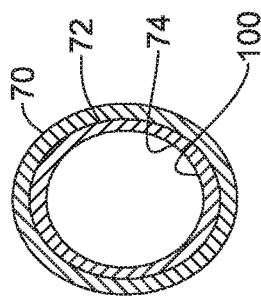
FIG. 11 is a cross-sectional view of the stent of FIG. 10 taken along line A-A showing an outer covering surrounding the tubular body of the stent.

The covering 70 may be disposed on external surfaces 72 of the tubular body of the stent 100, as depicted in FIG. 11, or disposed on the internal surfaces 74 of the tubular body of the stent 100, as depicted in FIG. 12, or on both the internal and external surfaces of the tubular body of the stent 100, thereby embedding the stent 100 in the polymeric material. FIGS. 11 and 12 are alternative cross-sectional views taken along line A-A of FIG. 10 looking toward the second end 110, without the retrieval and/or repositioning levers 140.

With any embodiment, the stent 100 may be used for a number of purposes including to maintain patency of a body lumen, such as in the coronary or peripheral vasculature, esophagus, trachea, bronchi colon, biliary tract, urinary tract, prostate, brain, and the like. The devices of the present invention may also be used to support a weakened body lumen or to provide a fluid-tight conduit for a body lumen.

Also, the stent 100 may be treated with any known or useful bioactive agent or drug including without limitation the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

Further, with any embodiment of the stent 100 the general tubular shape may be varied. For example, the tubular shape may have a varied diameter, may be tapered, and may have one or more outwardly flared ends and the like. Further, the ends of the stent 100 may have a larger diameter than the middle regions of the stent 100. In one particularly useful embodiment, at least one of the ends of the stent 100 may transition from one diameter to a larger diameter forming a flared end region. In some embodiments, both ends of the stent 100 may transition in this manner to yield "flared" end regions at the ends of the stent 100, as depicted in FIG. 10.

Various stent types and stent constructions may be employed for the stent 100. For example, the stent 100 may be a self-expanding stent or a balloon expandable stent. The stent 100 may be capable of radially contracting to a compressed or collapsed configuration for delivery, and then expandable to an expanded configuration during deployment in the body lumen. Thus, the stent 100 may be described as radially distensible or deformable. Self-expanding stents include those that have a spring-like action which causes the stent to radially expand, or stents which expand due to the memory properties of the stent material for a particular configuration at a certain temperature. The configuration of the stent may also be chosen from a host of geometries. For example, wire stents can be fastened into a continuous helical pattern, with or without a wave-like or zig-zag in the wire, to form a radially deformable stent. Individual rings or circular members can be linked together such as by struts, sutures, welding or interlacing or locking of the rings to form a tubular stent. In other embodiments, the stent 100 may be formed as a monolithic tubular member by etching or cutting a pattern of interconnected struts from a tube.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The invention's scope is, of course, defined in the language in which the appended claims are expressed.

The invention claimed is:

1. A braided stent comprising:
   a plurality of wires interwoven in a braided pattern to form a tubular stent body having a length between opposed atraumatic first and second open ends with each open end having a circumference;
   at least three repositioning and/or retrieval levers attached to the stent body at a plurality of discrete points, the repositioning and/or retrieval levers spaced apart around the circumference of the first open end, each repositioning and/or retrieval lever formed from a single continuous wire having a loop portion extending radially away from the tubular stent body and first and second legs extending along 25% or more of the length of the tubular stent body, wherein the loop portion is positioned between the first and second legs.

2. The braided stent of claim 1, wherein the first and second legs extend helically along interwoven wires of the braided pattern of the tubular stent body.

3. The braided stent of claim 1, wherein the repositioning and/or retrieval levers are made of a material having a greater stiffness than a material of the interwoven wires forming the tubular stent body.

4. The braided stent of claim 1, wherein the repositioning and/or retrieval levers extend radially outward from the tubular stent body at an angle of between 30 and 90 degrees from a central longitudinal axis of the tubular stent body.

5. The braided stent of claim 1, wherein the repositioning and/or retrieval levers are configured to translate a radially inward squeezing force applied to the loop portion of the repositioning and/or retrieval levers at a location beyond the first open end to a radially inward contracting force along the first and second legs extending along the tubular stent body.

6. The braided stent of claim 1, wherein the first open end of the stent body is defined by a plurality of closed loops, wherein the loop portions of the repositioning and/or retrieval levers extend longitudinally beyond the plurality of closed loops.

7. The braided stent of claim 1, wherein first and second terminal ends of the single continuous wire are positioned between the first and second open ends of the tubular stent body.

8. The braided stent of claim 1, wherein the plurality of repositioning and/or retrieval levers are separate elements from the plurality of interwoven wires forming the stent body.

9. The braided stent of claim 1, wherein the first and second legs of each of the repositioning and/or retrieval levers extend substantially over an entire length of the tubular body from the first open end to the second open end.

10. The braided stent of claim 1, wherein each of the first and second legs of each of the repositioning and/or retrieval levers extends helically along an interwoven wire of the plurality of interwoven wires forming the tubular body.

11. The braided stent of claim 10, wherein the first leg extends in a first helical direction and the second leg extends in a second helical direction opposite the first helical direction.

12. The braided stent of claim 1, wherein the first and second legs of each of the repositioning and/or retrieval levers are interwoven through the tubular body.

13. The braided stent of claim 1, wherein each of the first and second legs of each of the repositioning and/or retrieval levers is attached to an interwoven wire of the plurality of interwoven wires forming the tubular body at a plurality of welds.

\* \* \* \* \*